United States Patent [19]

Gillot

[11] 4,302,772

[45] Nov. 24, 1981

[54] DEVICE FOR THE TELEVISUAL INSPECTION OF THE INNER SURFACE OF A CLOSED CYLINDRICAL VESSEL

[75] Inventor: Georges Gillot, Wasquehal, France

[73] Assignee: Framatome, Wasquehal, France

[21] Appl. No.: 135,853

[22] Filed: Mar. 28, 1980

[30] Foreign Application Priority Data

Mar. 30, 1979 [FR] France .............................. 79 08005

[51] Int. Cl.³ .............................................. H04N 7/18
[52] U.S. Cl. .................................................. 358/100
[58] Field of Search .................. 358/98, 99, 100, 108, 358/210; 176/19 R

[56] References Cited

U.S. PATENT DOCUMENTS 3,764,736  10/1973  Kosky et al. ....................... 358/100

OTHER PUBLICATIONS

Keller et al.-In-Service Inspection Tool for Nuclear Reactor Vessels, Instn. Mech. Engrs., C47/72-Conf. on Periodic Inspect. of Pressure, London, Eng., May 1972, pp. 126-139.

Primary Examiner—Joseph A. Orsino, Jr.
Attorney, Agent, or Firm—Haseltine and Lake

[57] ABSTRACT

The invention relates to a device for the televisual inspection of the inner surface of a closed cylindrical vessel having a vertical axis and having an access hole in its upper part. The device comprises a television camera and at least one floodlight for lighting the area to be inspected. The camera is suspended from a flexible tube which is rigid under torsion and through the inside of which pass electricity supply cables for the camera and the floodlight. The flexible tube is guided and orientated over its path from the outside into the interior of the vessel by a rigid tubular guide, and means are provided for causing the flexible tube to rotate about its axis, for releasably holding the tube and the camera against axial movement, for precisely identifying angular and vertical positions of the camera, and for centering the camera in the vessel.

The device is particularly applicable to the inspection of pressurizers of a pressurized water nuclear reactor.

6 Claims, 5 Drawing Figures

DEVICE FOR THE TELEVISUAL INSPECTION OF THE INNER SURFACE OF A CLOSED CYLINDRICAL VESSEL

The invention relates to a device for the televisual inspection of the inner surface of a closed cylindrical vessel having a vertical axis and having an access hole in its upper part.

In the field of nuclear power station construction, it is necessary to monitor the condition of the inner lining of vessels of large size and more particularly of considerable height which comprise only one opening or manhole in their upper part. For example, it is necessary to carry out inspection of the inner lining of the pressurizers disposed in the primary circuit of the reactor to regulate the water pressure in this circuit.

In the case of currently made pressurized water nuclear reactors, the pressurizer takes the form of a cylindrical vessel closed by two spherical end members or caps and close to 12 m in height, the bottom end cap comprising bushings for the insertion of heater rods while the top end cap comprises a manhole or closeable aperture to allow access to the interior of the pressurizer for purposes of maintenance or repairs.

It is necessary to check the condition of the inner lining of the pressurizer in its cylindrical part from the top plate for servicing the heater rods as far as the seam connecting the upper hemispherical end cap to the cylindrical body of the pressurizer.

This inspection operation is carried out by means of a camera, provided with one or a plurality of floodlights which make it possible to illuminate the inside of the pressurizer which is introduced through the opening in the top end cap of the pressurizer and suspended from the supply cable of the camera.

The camera head is equipped with a rotary mirror for radial viewing of the entire inner surface of the pressurizer. The mirror is caused to rotate by an associated electric motor mounted on the camera.

Such a system has certain drawbacks because setting the motor in rotation produces a pendular movement of the camera and therefore provides poor stability of the picture.

Furthermore, the image obtained by reflection in the mirror is a reversed image of the wall of the pressurizer, and since the mirror is driven so as to perform a continuously rotary movement, the picture is a moving picture and the details therein can be precisely studied only with difficulty. For all these reasons, the effective field of view is small, which means that the operations of inspecting the inner surface of the pressurizer are difficult.

Similarly, it is not possible with currently existing devices to know the exact level of the picture transmitted by the camera and its angular position at a given moment.

It is an object of the invention to provide a device which allows inspection of the inner surface of the vessel by supplying a stable picture corresponding to a considerable portion of the inner surface of the vessel and whose position is easily identifiable both with regard to its level and with regard to its angular position.

According to the invention there is provided a device for the televisual inspection of the inner surface of a closed cylindrical vessel having a vertical axis and having an access hole in its upper part, said device comprising:

a television camera;
at least one floodlight for lighting the area to be inspected;
a flexible tube;
means suspending said camera and said floodlight from one of the ends of said flexible tube;
a rigid tubular guide for extending into the vessel through the access hole, and having a terminal portion which is, in use, arranged vertically within the vessel for guiding and orientation of said flexible tube over its path from the outside into the vessel;
drive means for causing rotation of said flexible tube about its axis and situated in use outside the vessel;
means for holding said tube and said camera against axial movement, said means being releasable for permitting vertical displacement of said camera and being located in use outside the vessel;
means for indicating the angular position and vertical position of said camera; and
centering means situated above said camera and free to rotate and for bearing on the wall of the vessel;
wherein said flexible tube is torsionally rigid so that it can accurately transmit to said camera rotary movements from said drive means.

An embodiment of a televisual inspection device according to the invention, applicable to the inspection of the inner surface of a pressurizer of a pressurizer water nuclear reactor, will now be described by way of example only, with reference to the drawings.

In the drawings:

FIG. 1 shows part of the substantially hemispherical top part or cap 1 of a pressurizer of a nuclear reactor employing pressurized water which is provided with a manhole or opening 2 on which is located a support of a device for inspecting the inner surface of the pressurizer which will be described hereinafter.

Figure 1:
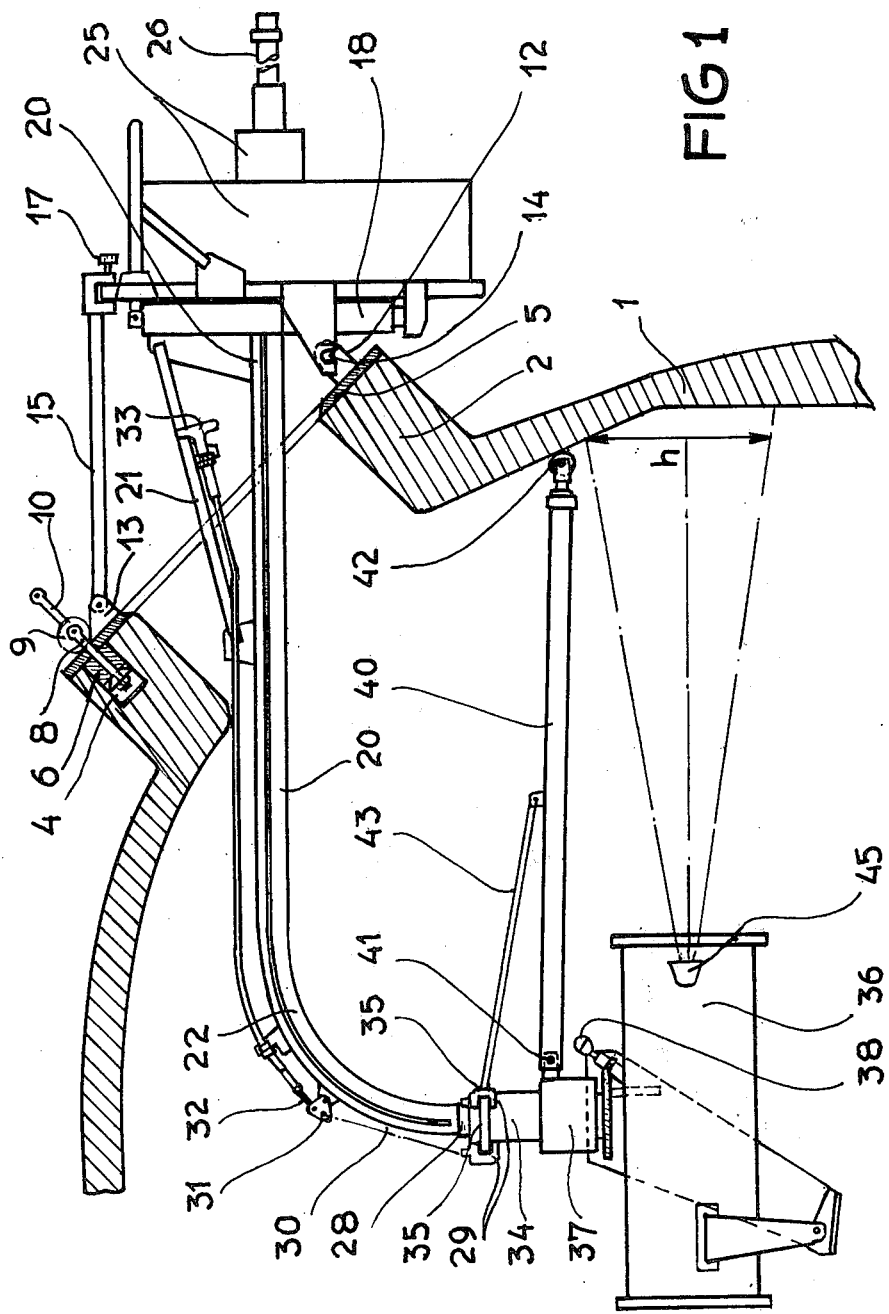
FIG. 1 shows an elevational view of an embodiment of an inspection device according to the invention in its working position in a nuclear reactor pressurizer which is shown in section.

The support is fixed using bolt holes such as hole 4 which are used for fixing the plate which closes the opening 2, when the pressurizer is in use.

The support of the inspection device comprises a crown 5 which is removably fixed over the opening 2 by introducing into the bolt holes 4 rubber blocks, such as block 6, each traversed by a fixing screw 8 connecting the block through the crown 5 to a cam 9 which is operated by a handle 10 to radially expand the rubber block to fix the crown in position to remove the pressure on the rubber block for demounting the device.

Mounted on the crown 5 are supports, such as supports 12 and 13, the supports 12 being integral with spindles 14 on which a frame 18 of the inspection device rests, and the supports 13 carrying in articulated manner arms 15, the other ends of which are connected to the upper part of the frame 18 by means of milled screws 17.

A rigid tubular guide or duct 20 is fixed on the frame 18 by a structure 21 and penetrates into the opening 2 in the pressurizer horizontally as far as the level of an elbow 22 which permits the end of the guide duct 20 to assume a vertical direction inside the vessel.

The frame 18 also carries an assembly 25 for rotating a flexible tube 26 carrying a camera 36. The end of the tube 26 located outside the vessel can be seen in FIG. 1.

The assembly 25 also comprises means for axially locking the flexible tube 26 to prevent translatory movements thereof which would produce a vertical movement of the camera inside the vessel.

The assembly 25 will be described in greater detail with reference to FIG. 2.

At its end which is located inside the vessel, the guide duct 20 is provided with a socket 28 on which are fixed hooks 29 articulated about horizontal axes, and which can be rotated about these axes by pulling on a cable 30 connected to an operating member 31 which is itself operated by a cable 32 connected at its end to a handle 33 disposed outside the vessel, and which makes it possible to operate the hooks 29 from a position close to the opening in the upper part of the pressurizer. When they are in their lower position, the hooks 29 are in engagement with a collar 35 disposed on the upper part of a tubular member 34 which, when it is in the position shown in FIG. 1 in which the hooks 29 connect it to the socket 28, is an extension of the vertical part of the guide duct 20 and allows free passage of the flexible tube 26 which carries the camera 36 at its end which is inside the vessel.

The camera 36 is connected to the end of the tube 26 via a tubular support 37, the lower part of which permits removable attachment of the camera by means of a hooking lever 38. The electricity supply and other cables for the camera pass through the tube 26. The tube 26 is constituted by an inner tubular part having corrugations to facilitate deformation of the tube by flexion, for example at the level of the elbow 22 in the guide duct 20, and an outer layer consisting of a double metal braid which improves the strength of the tube.

Such a tube which is extremely strong and which is commercially available makes it possible to suspend the camera in an extremely safe manner and to cause the camera suspension tube to follow a path in which there are bends such as the elbow 22 in the guide duct 20.

Such a tube also makes it possible to transmit rotary movements along its length in an extremely accurate manner, the tube undergoing virtually no deformation when subjected to moderate torsion stresses.

The support 37 of the camera and the tubular member 34 carry a centering device which consists of three arms such as arm 40 articulated at 41 on the support 37 and comprising at the end which is not connected to the support 37 one or more rollers 42 intended to contact the inner surface of the vessel during movements of the camera.

Each of the arms 40 is connected to a rod 43 articulated at one of its ends on the arm 40 and at its other end on the collar 35 of the tubular member 34.

The base of the member 34 is fitted over the upper part of the support 37 when the camera is in the fully raised position as shown in FIG. 1. In this position, the arms 40 are deployed in such a way that the rollers 42 are in contact with the inner surface of the pressurizer vessel.

We will see hereinafter, in the description of FIGS. 3, 4 and 5, how the device for deploying the arms 40 functions when the camera is introduced into the pressurizer.

The camera 36 carries in its upper part two floodlights 45 which make it possible to illuminate the zone inspected by the camera.

The means for rotating the flexible tube carrying the camera and the means which locks this tube against translatory movement will now be described, reference being made to FIG. 2.

Figure 2:
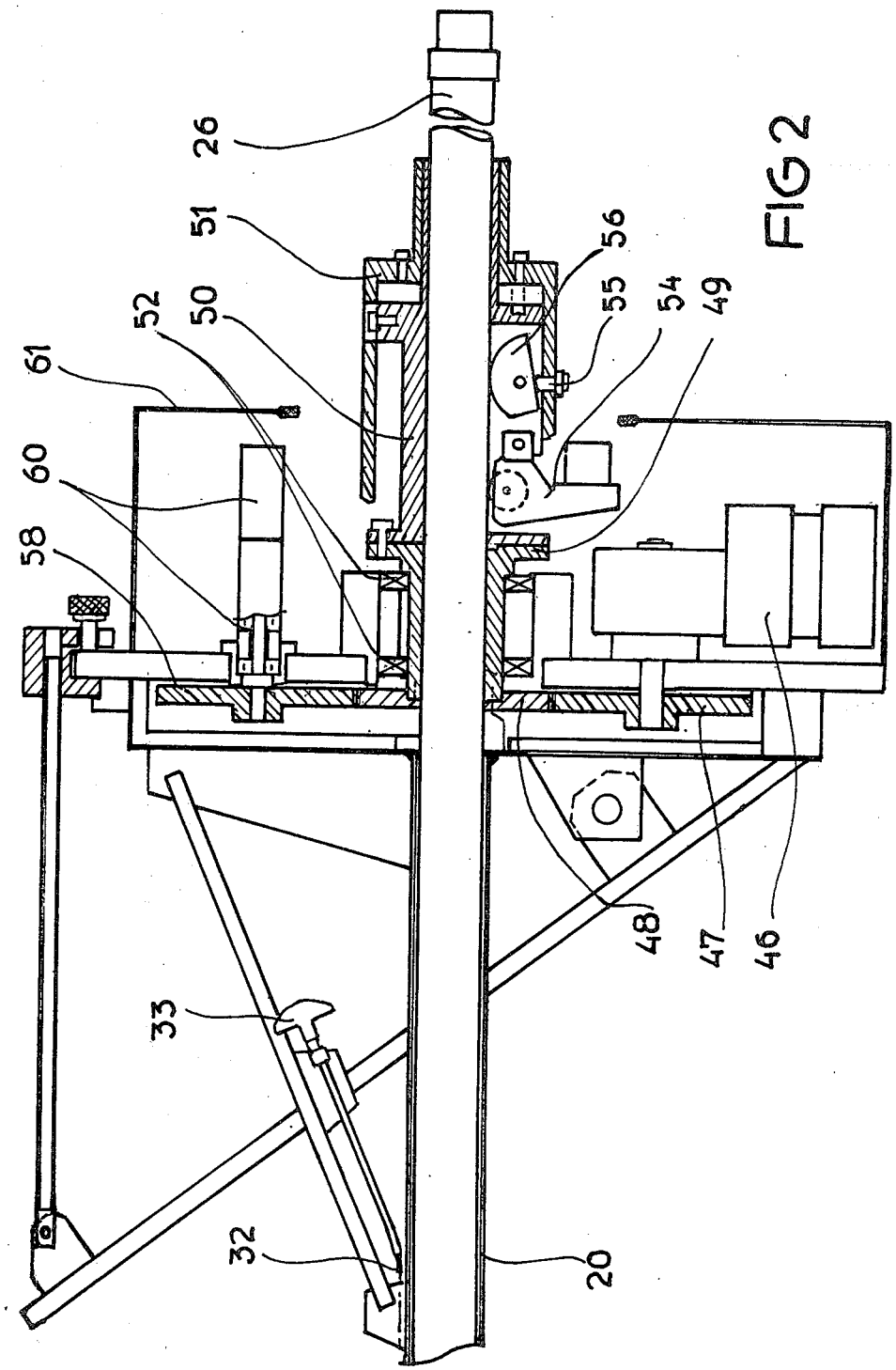
FIG. 2 shows a vertical sectional view of the means used in the embodiment of FIG. 1 for producing rotary movement, locking the camera and identifying its position.

FIG. 2 shows in cross-section and on a larger scale than in FIG. 1 the mounting of the flexible tube 26 at the level of the assembly 25 for producing the rotary movement and for locking. The device which produces the rotary movement consists of a motorized reduction gearing 46, the output shaft of which is integral with a pinion 47 meshing with a pinion 48 which is itself integral with a movable assembly comprising three parts 49, 50 and 51.

The part 49 is a sleeve integral with the pinion 48 an which is rotatably mounted, by means of bearings 52, in the frame of the means for producing the rotary movement. The part 50 integral with the tubular sleeve 49 carries a device 54 for accurately determining the vertical position of the camera as will be described hereinafter. The tubular member 50 also carries the device for locking the flexible tube against translatory movement which consists of the sleeve 51 which is mounted to slide on the tubular member 50 and is provided with a screw 55, whose end, directed towards the inside of the sleeve 51, comes into contact, during movements of the sleeve 51 in one axial direction relative to the member 50, with an eccentrically mounted member 56 for locking the flexible tube 26. Thus axial movement of the sleeve 51 in one direction will bring the locking member 56 into a clamping position against the flexible tube 26, and, in the other direction, will bring the member 56 to a position which permits free displacement of the tube 26 inside the tubular member 50.

In reality, three locking devices similar to the device 55, 56 are disposed at regular intervals over the circumference of the sleeve 51.

It will be seen therefore that by simple axial movement of the member 50, performed manually, the flexible tube 26 becomes locked inside the member 50, preventing axial movement of the tube 26 inside the guide duct 20 and therefore preventing vertical movement of the camera inside the vessel.

In this position, in which the tube 26 is fixed relative to the tubular member 50 and the sleeve 49, the tube 26 can be rotated by operation of the motorized reduction gearing 46.

The pinion 48 also drives a secondary pinion 58 which itself drives a visual coding system which makes it possible to measure with extreme accuracy the angular position of the tube 26 and therefore of the camera, and since the tube 26 is not readily deformable under torsion, the camera accurately follows the rotary movements of the flexible tube 26 inside the vessel. Indeed, the torsion stresses necessary to cause the camera to rotate are extremely small and under these stresses, the tube 26 does not suffer any deformation so that rotation of the tube 26 is exactly reproduced by the camera.

The measurement carried out at the level of the optical coder 60 thus permits extremely accurate knowledge of the angular position of the camera inside the vessel.

The motorized reduction gearing 46 and the pinions 47 and 48 are provided in such a way that the amplitude of rotation of the camera may be 370° before there is a reversal of the direction of rotation, this rotation, which is slightly in excess of a complete turn, making it possible to achieve a scan with a slight overlap, guaranteeing a total scanning of the inner surface of the vessel of the pressurizer at any level at which the camera is located.

The motorized reduction gearing 46, which is fitted with a variable speed device, makes it possible to achieve a very slow rotation of the camera with facility for changing to fairly fast speeds if required.

Therefore, for each level at which the camera is located, it is possible to carry out an inspection of the wall over a height h shown in FIG. 1.

When inspection is completed over a band of height h, the sleeve 51 is moved axially to release the tube 26 and the camera is moved to a fresh level by manually manipulating the tube 26 either to raise or lower the camera. The vertical position or level indicating device 54, which comprises rollers which are caused to rotate when the tube 26 performs a translatory movement, makes it possible to read directly the position of the camera in terms of level in the vessel, with a very high degree of accuracy.

It is thus possible of carry out a vertical sweep over the entire vessel of the pressurizer by carrying out successive vertical displacements of the camera with an overlap between each of the heights h viewed, this overlap being possibly of the order of 1 mm for example.

The assembly which produces rotary movement of the camera is protected by a cover 61 which leaves visible the level indicating meter which the operator has to consult when positioning the camera at the various levels at which inspection is to be carried out.

The operation of the centering device will now be described with reference to FIGS. 3, 4 and 5.

Figure 3:
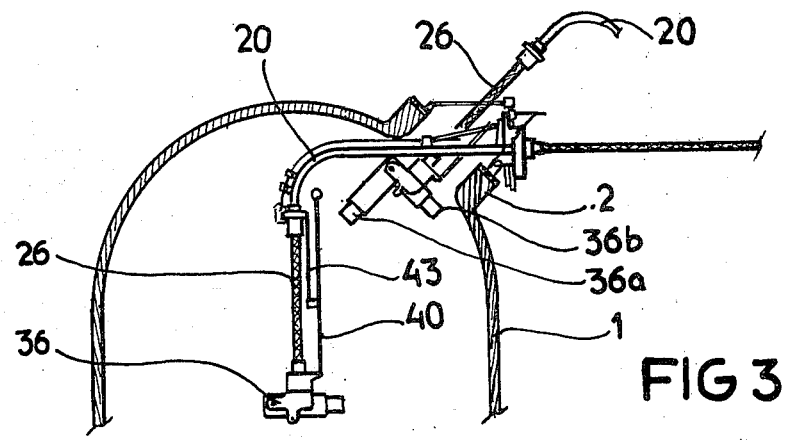
FIGS. 3, 4 and 5 show the device of FIG. 1 in different positions inside the vessel of the pressurizer at the time of locating the centering device carried by the camera.

FIG. 3 shows the whole device comprising the flexible tube 26 and the camera 36 in two positions 36a, 36b, the position 36a corresponding to a position during introduction of the camera through the opening 2 while the position 36b corresponds to the working position of the camera.

When the inspecting device is introduced into the pressurizer, the camera is in position 36a and the tube 26 extends from the guide duct 20 by a certain length permitting maintenance of the centering device in a folded back position, the tubular member 34 being connected to the end of the guide duct 20, the hooks 29 being in positions of engagement with the collar 35 of the member 34.

The camera, its flexible support tube 26 and the guide duct 20 are then placed inside the vessel 1, in the manner illustrated in FIG. 3, the centering device 40 still being in a folded back position. The support crown 5 is then fixed to the opening 2 by virtue of the fixing devices 6, 8, 9 which have been described above.

Figure 4:
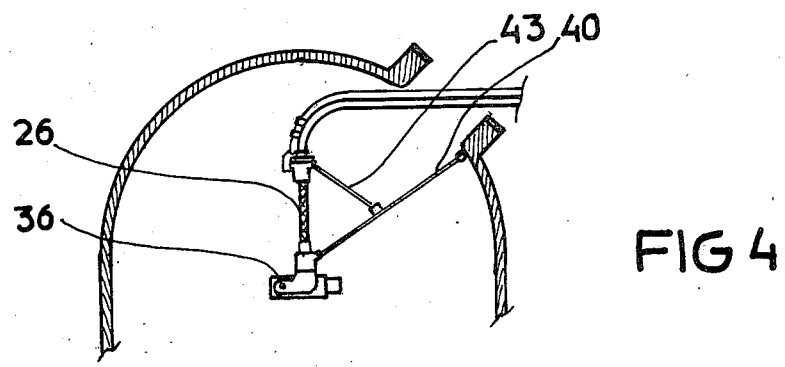

After having released the device 51, 55, 56 which maintains the tube in position against translatory movements, the camera is raised manually by pulling on the tube 26 as is illustrated in FIG. 4. The articulating rods 43 make it possible to fold back the arms 40.

Figure 5:
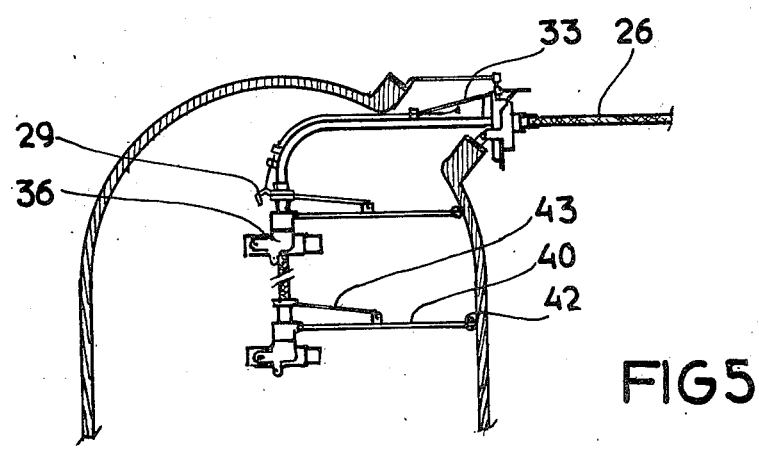

When the camera is fully raised, as can be seen in the top part of FIG. 5, the hooks 29 are released by pulling on the handle 33 which is accessible from the operating station outside the vessel.

Releasing the hooks 29 frees the tubular member 34 from the duct 20, the member 34 coming to rest on the top part of the support 37 of the camera 36.

When the camera is lowered by allowing the tube 26 to move in the guide duct 20 under the effect of the weight of the camera, the tubular member 34 accompanying the camera and its support as they move maintains the arms 40 of the centering device in a deployed position in which the rollers 42 are in contact with the inside wall of the pressurizer.

In order to have a lightweight and rigid centering device, aluminum tubes are used for the arms 40.

For any of its levels, the camera will thus be centered in the pressurizer, the length of the arms being such that when the arms are fully deployed, the rollers 42 are in contact with the inside surface of the pressurizer for each of the three arms, at the location of the maximum diameter of the vessel.

When inspection of the pressurizer is completed and the camera has been raised again, the hooks 29 are reset in position to connect the tubular member 34 with the base 35 of the guide duct 20, after which the camera is lowered again on the tube 26 by a sufficient amount to allow the centering device to be folded back fully before removing the support crown from the opening 2 of the pressurizer. It is then sufficient to slide the duct 20 through the opening in order to remove the camera which can be placed manually in position 36a so that it can be fully withdrawn through the opening 2 in the pressurizer 1.

For the operations connected with inspecting the pressurizers of currently constructed pressurized water reactors, it is necessary to have a flexible tube with an inner sheath of corrugated stainless steel of close to 12 mm length.

Inspection is generally carried out from the bottom of the pressurizer upwardly, the camera being raised by successive steps as has been explained hereinabove.

For lighting of the zone being inspected, generally two floodlights are used which are supplied with a low voltage current and which are situated one on either side of the camera in a horizontal plane located at the level of the objective.

Thus the picture transmitted directly to the operator who is in charge of inspection provides an immediate and effective means of monitoring every one of the zones explored by this camera.

Identification of the zones inspected is extremely accurate because the optical coder 60, as the camera rotates, can emit data every tenth of a degree of the angle of rotation of this camera so that all the successive positions are exactly marked.

Similarly, the level of the camera is known to a high degree of accuracy by virtue of the roller device 54.

The advantages of the above described device which are clearly evident from the description of the inspection device are that by virtue of the flexible tube which is non-deformable under torsion, the device for rotating the camera located outside the vessel transmits known rotations with a very high degree of accuracy and without giving rise to secondary movements of the camera, that this position is fixed accurately in the radial direction by virtue of the centering device and that the level is itself known in a very accurate manner.

In this way, a stable picture is obtained and the position of this picture inside the vessel is fully identified.

Furthermore, the structure of the device and its operation are particularly simple, so much so that the operations of inspecting the inner lining of the pressurizer can be carried out in a relatively short time.

However, the invention is not limited to the form of embodiment which has just been described; on the contrary, it comprises all possible variations thereof and it is possible to conceive of modifications in points of detail without thereby departing from the scope of the invention.

For example, a device has been described in which the vertical movements were produced manually but it is equally possible for these movements to be motorized, for example by means of a friction wheel drive engaging the flexible tube for translatory movements of this tube.

Centering means have been described which comprise particularly simple articulated arms but it is equally possible to conceive of other centering devices employing mechanical, hydraulic or pneumatic means other than the means described.

Similarly, the means of identifying the angular position and the level of the camera may be of a type other than those which have been described.

The means of guiding the flexible tube may take a form other than that envisaged in the description and its method of mounting on the opening in the vessel to be inspected may likewise be different.

The flexible tube described, comprising an inner sheath of stainless steel in which there are corrugations allowing the tube to be satisfactorily deformed under flexion and to have considerable strength under torsion, may be replaced by any other flexible tube which has sufficient rigidity under torsion for it accurately to transmit to the camera the rotary movements of the drive means.

Finally, the device according to the invention may be applied not only to the inspection of a pressurizer of a pressurized water nuclear reactor but also to the inspection of any closed cylindrical vessel of large size, which has a vertical axis and which has an access hole in its upper part, such vessels possibly being used in the chemical industry or in the energy production industry. This device may be used in all boiler-making activities.

What is claimed is:

1. A device for the televisual inspection of the inner surface of a closed cylindrical vessel having a vertical axis and having an access hole in its upper part, said device comprising:
   television camera;
   at least one floodlight for lighting the area to be inspected;
   a flexible tube;
   means suspending said camera and said floodlight from one of the ends of said flexible tube;
   a rigid tubular guide for extending into the vessel through the access hole, and having a terminal portion which is, in use, arranged vertically within the vessel for guiding and orientation of said flexible tube over its path from the outside into the vessel;
   drive means for causing rotation of said flexible tube about its axis and situated in use outside the vessel;
   means for holding said tube and said camera against axial movement, said means being releasable for permitting vertical displacement of said camera and being located in use outside the vessel;
   means for indicating the angular position and vertical position of said camera; and
   centering means situated above said camera and free to rotate and for bearing on the wall of the vessel;
   wherein said flexible tube is torsionally rigid so that it can accurately transmit to said camera rotary movements from said drive means.

2. A device according to claim 1, wherein said centering means comprises an assembly of arms, preferably three arms, each articulated at one of its ends on the camera or support means therefor and carrying at its other end a roller rotatable about a horizontal axis, the lengths of said arms being such that when said camera is centered each said roller is in contact with the inside wall of the vessel, and rods each articulated at one of its ends on a respective said arm and at its other end on a tubular member disposed around said flexible tube and having a diameter larger than that of said flexible tube, said tubular member being adapted to be releasably fixed to the end of said terminal portion of said tubular guide by an assembly of hooks which can in use be manipulated from outside the vessel.

3. A device according to claim 1 or claim 2, wherein said flexible tube comprises a tubular sheath of stainless steel provided with corrugations having as their axis the axis of the tube, said sheath being easily deformable in flexion but rigid in torsion.

4. A device according to claim 1, wherein two floodlights are disposed one on each side of said camera in a horizontal plane located at the level of the objective of said camera.

5. A device according to claim 1, wherein said drive means comprise a motorized reduction gearing connected to drive an assembly of pinions of which one is integral with a rotatable assembly which can be made integral with said flexible tube.

6. A device according to claim 5, wherein one of the pinions of said assembly of pinions is connected to an optical coding device for indicating the angular position of said camera.

* * * * *